US012623215B2

(12) United States Patent
Bresson et al.

(10) Patent No.: US 12,623,215 B2
(45) Date of Patent: May 12, 2026

(54) METHOD FOR PREPARING A MONOLITHIC SUPPORT ON WHICH URANYL CATIONS ARE IMMOBILISED, AND ASSOCIATED METHODS FOR CAPTURE AND RECOVERY

(71) Applicants:COMMISSARIAT À L'ENERGIE ATOMIQUE ET AUX ÉNERGIES ALTERNATIVES, Paris (FR); CENTRE NATIONAL DE LA RECHERCHE SCIENTIFIQUE, Paris Cedex (FR); UNIVERSITE PARIS-SACLAY, Gif-sure-Yvette (FR)

(72) Inventors: Carole Bresson, Palaiseau (FR); Marta Garcia-Cortes, Oviedo (ES); Claude Vidaud, Piolenc (FR); Thuy Tran, Verrieres le Buisson (FR)

(73) Assignees: COMMISSARIAT À L'ENERGIE ATOMIQUE ET AUX ÉNERGIES ALTERNATIVES, Paris (FR); CENTRE NATIONAL DE LA RECHERCHE SCIENTIFIQUE, Paris Cedex (FR)

( * ) Notice: Subject to any disclaimer, the term of this patent is extended or adjusted under 35 U.S.C. 154(b) by 1066 days.

(21) Appl. No.: 17/753,707

(22) PCT Filed: Sep. 7, 2020

(86) PCT No.: PCT/FR2020/051537

§ 371 (c)(1),
(2) Date: Mar. 11, 2022

(87) PCT Pub. No.: WO2021/048488

PCT Pub. Date: Mar. 18, 2021

(65) Prior Publication Data

US 2022/0339628 A1 Oct. 27, 2022

(30) Foreign Application Priority Data

Sep. 12, 2019 (FR) ...................................... 1910077

(51) Int. Cl.
| | |
|---|---|
| *B01L 3/00* | (2006.01) |
| *B01J 20/28* | (2006.01) |
| *B01J 20/286* | (2006.01) |
| *B01J 20/32* | (2006.01) |
| *C01G 43/025* | (2006.01) |
| *C07K 1/04* | (2006.01) |

(52) U.S. Cl.
CPC ... *B01L 3/502707* (2013.01); *B01J 20/28042* (2013.01); *B01J 20/286* (2013.01); *B01J 20/321* (2013.01); *B01J 20/3221* (2013.01);

*C01G 43/025* (2013.01); *C07K 1/045* (2013.01); *B01J 2220/54* (2013.01); *B01J 2220/82* (2013.01); *C01P 2006/44* (2013.01)

(58) Field of Classification Search
CPC .................................................. B01J 20/28042
See application file for complete search history.

(56) References Cited

U.S. PATENT DOCUMENTS

2010/0144044 A1* 6/2010 Mollegaard ........ C07K 14/4732
436/86
2014/0178252 A1 6/2014 Hatch et al.

FOREIGN PATENT DOCUMENTS

WO 2019008278 A1 1/2019

OTHER PUBLICATIONS

International Search Report for PCT/FR2020/051537 dated Dec. 3, 2020 and translation thereof.
Written Opinion for PCT/FR2020/051537 dated Dec. 3, 2020.
Basset, Christian et al. "Specific capture of uranyl protein targets by metal affinity chromatography", Journal of Chromatography A, Elsevier, Feb. 2, 2008, vol. 1185, No. 2, pp. 233-240.
Dedieu, Alain et al. "Identification of uranyl binding proteins from human kidney-2 cell extracts by immobilized uranyl affinity chromatography and mass spectrometry", Journal of Chromatography A, Elsevier, 2009, vol. 1216, pp. 5365-5376.
Araya-Farias, Monica et al. "A lab-on-a-chip for monolith-based preconcentration and electrophoresis separation of phosphopeptides", 2017, vol. 142, pp. 485-494.

* cited by examiner

*Primary Examiner* — Michael F Pepitone
(74) *Attorney, Agent, or Firm* — Chrisman Gallo Tochtrop LLC

(57) ABSTRACT

A method for preparing, in the internal volume of at least one channel, a monolithic support on which uranyl cations are immobilised. The method comprises: (a) activating the inner surface of the channel(s); (b) introducing, into the internal volume of the channel(s), a polymerisation solution comprising: a monomer comprising a phosphate group, at least one crosslinking agent, several solvents, and a radical polymerisation initiator; (c) polymerising the polymerisation solution; (d) rinsing the monolithic support obtained in step (c); and (e) contacting the monolithic support previously rinsed, with a solution comprising uranyl cations. A method for capturing proteins that selectively bind uranium by means of a monolithic support prepared by the abovementioned method, as well as to a method for recovering proteins that selectively bind uranium with the capture method.

20 Claims, No Drawings

METHOD FOR PREPARING A MONOLITHIC SUPPORT ON WHICH URANYL CATIONS ARE IMMOBILISED, AND ASSOCIATED METHODS FOR CAPTURE AND RECOVERY

CROSS-REFERENCE TO RELATED APPLICATIONS

This is a National Stage application of PCT international application PCT/FR2020/051537, filed on Sep. 7, 2020, which claims the priority of French Patent Application No. 1910077, filed Sep. 12, 2019, both of which are incorporated herein by reference in their entirety.

TECHNICAL FIELD

The present invention is concerned with a method for preparing a monolithic support on which uranyl cations are immobilised, this monolithic support being more particularly synthesised and anchored in situ into the channel(s) of a miniaturised analytical system.

The present invention is also concerned with a method for capturing proteins that selectively bind uranium which is immobilised on such a monolithic support.

Finally, the invention is concerned with a method for recovering proteins that selectively bind uranium, this recovery method implementing the previous capture method.

STATE OF PRIOR ART

Neurotoxic effects induced by low concentrations of uranium are suspected in humans. Although the biodistribution of uranium in the human body is well described, biochemical mechanisms that occur at the cellular and molecular level and that would be responsible for these neurotoxic effects have yet to be elucidated. The identification of target molecules, in particular proteins that selectively bind uranium, in a human neuronal cell model, should make it possible to predict the uranium-protein species that are likely to be formed and to describe in detail the biochemical mechanisms associated with uranium neurotoxicity.

To identify such target molecules, the publication by C. Basset et al. ("*Specific capture of uranyl protein targets by metal affinity chromatography*", Journal of Chromatography A, 2008, 1185, 233-240), referenced [1] at the end of the present description, described the exploitation of the immobilised metal affinity chromatography (IMAC) separation mode in order to selectively capture the proteins binding uranium in its uranyl form $UO_2^{2+}$.

In the following of the present description, the expression "uranium-selectively binding proteins" may be used instead of "proteins that selectively bind uranium in its uranyl form $UO_2^{2+}$".

In publication [1], the selective capture experiments, based on the IMAC mode, were conducted with a support formed by styrene-divinylbenzene copolymer microbeads functionalised with aminophosphonate groups (Duolite® C467) through which the uranyl ions were immobilised. The presence of the aminophosphonate groups proved satisfactory for immobilising, by complexation, the uranyl ions and retaining free uranyl bonds that bind with proteins, and in particular the uranium target proteins contained in samples of human complex serum.

As reported in the publication by A. Dedieu et al. ("*Identification of uranyl binding proteins from human kidney*-2 cell extracts by immobilized uranyl affinity chromatography and mass spectrometry", Journal of Chromatography A, 2009, 1216, 5365-5376), referenced [2], the support described in publication [1] was used for the capture and identification of uranium-selectively binding proteins contained in extracts of human kidney cells HK-2. These proteins were captured in batch mode and then identified by proteomics.

Publications [1] and [2] therefore report the first works that have been carried out to immobilise $UO_2^{2+}$ ions for the capture of uranium-selectively binding proteins and their identification.

However, the capture as well as the identification of uranium target proteins present in cell extracts are still challenging, insofar as these cell extracts are only available in very limited amounts. Consequently, the target proteins are only present in these cell extracts in low abundance. Furthermore, the batch capture method requires the use of a minimum volume of 50 µL of microbeads in a suspension system, which in turn requires the involvement of 20 µg to 50 µg of protein samples. One of the major direct consequences is the difficulty in carrying out experimental replicates, which are essential to validate repeatability of the capture method, but also of the identification, of these uranium target proteins contained in these cell extracts.

There is therefore an imperative need to reduce the scale of the uranium target protein capture method given the very low availability of biological samples, the low abundance of these target proteins and the limitations of the batch mode.

However, the miniaturisation of a support formed by microbeads presents a certain number of technical obstacles: not only filling the channels of miniaturised analytical systems with microbeads is, on the one hand, laborious and, on the other hand, not very reproducible, but it furthermore requires the installation of frits for maintaining these microbeads. However, the frits may be the cause of the formation of air bubbles and/or of solute adsorption phenomena during analyses. All these elements generate significant reproducibility problems for selective capture experiments.

The purpose of the present invention is, therefore, to overcome the drawbacks of prior art and to provide a method for preparing a support on which $UO_2^{2+}$ cations are immobilised, this support allowing the continuous capture of uranium-selectively binding proteins contained in a biological sample regardless of its volume.

It is a further purpose of the present invention to provide a method for capturing proteins that selectively bind uranium, these proteins being contained in a biological sample, this method having improved repeatability and robustness in comparison with those of the capture methods described in publications [1] and [2].

DISCLOSURE OF THE INVENTION

The previously set out and other purposes are achieved, firstly, by a method for preparing a support on which $UO_2^{2+}$ cations are immobilised, more particularly by a method for preparing, in the internal volume of at least one channel of a miniaturised analytical system, a monolithic support on which $UO_2^{2+}$ cations are immobilised.

According to the invention, this method comprises the following successive steps (a) to (e) of:
   (a) activating the inner surface of the channel(s);
   (b) introducing a polymerisation solution for synthesising a monolithic support into the internal volume of the channel(s), the polymerisation solution comprising:
      a monomer comprising a phosphate group, at least one crosslinking agent, several solvents, and a radical polymerisation initiator;

(c) polymerising the polymerisation solution obtained in step (b), whereby a monolithic support anchored onto the walls of the channel(s) is obtained;

(d) rinsing the monolithic support obtained in step (c); and (e) contacting the rinsed monolithic support obtained in step (d) with a solution comprising $UO_2^{2+}$ cations, whereby the monolithic support on which $UO_2^{2+}$ cations are immobilised is obtained.

The choice of this monomer comprising a phosphate group, in combination with a crosslinking agent, the solvents and the radical polymerisation initiator, allows the preparation, in a localised in situ manner, in the internal volume of the channel(s) of the miniaturised analytical system, of a monolithic support having a mechanically and chemically stable porous three-dimensional polymeric structure on which $UO_2^{2+}$ cations are immobilised.

As previously indicated, the method for preparing a monolithic support on which $UO_2^{2+}$ cations are immobilised according to the invention comprises the successive steps (a) to (e).

The activation step (a) has the effect of functionalising the inner surface of the channel(s) so as to allow subsequent anchoring of the monolithic support onto its or their inner walls.

In the case where the channel(s) is/are made of glass, the activation step (a) can be carried out by silanisation. Indeed, the silanisation reaction makes it possible to modify the silanol groups of the inner surface of the glass channels into vinyl groups.

For example, it can be contemplated to use gamma-methacryloxy-propyltrimethoxysilane (γ-MAPS) as a silanising agent.

The polymerisation solution for synthesising the monolithic support that is introduced into the internal volume of the channel(s) in step (b) of the preparation method according to the invention may be made by a mixture of the monomer comprising a phosphate group, the crosslinking agent(s), the solvents and the radical polymerisation initiator.

The polymerisation solution generally comprises a single monomer comprising a phosphate group.

This monomer may especially be selected from methacrylate monomers comprising a phosphate group or any other monomer which makes it possible to covalently bond a phosphate group to the surface of a monolithic solid support.

In one variant of the preparation method according to the invention, the proportion by mass of the monomer comprising a phosphate group, based on the total mass of the polymerisation solution, is between 4 mass % and 10 mass %.

It is set out that expressions "is between . . . and . . . " and "comprises from . . . to . . . " which are used in the present application are to be understood as defining not only the values of the range, but also the values of the limits of this range.

More particularly advantageously, the mass proportion of the monomer comprising a phosphate group, based on the total mass of the polymerisation solution, is between 8.7 mass % and 9.7 mass %.

In one preferential variant of the preparation method according to the invention, the polymerisation solution implemented in step (b) comprises a methacrylate monomer comprising a phosphate group, this methacrylate monomer being, even more preferentially, polyethylene glycol methacrylate phosphate (EGMP).

The polymerisation solution implemented in step (b) of the preparation method according to the invention additionally comprises at least one crosslinking agent.

In other words, the polymerisation solution may comprise only one crosslinking agent, but may just as well comprise a mixture of two, three or more crosslinking agents.

This or these crosslinking agents may especially be selected from a mixture of acrylamide (AA) and of bisacrylamide (BAA), bisacrylamide (BAA), ethylene dimethacrylate and an ethylene dimethacrylate derivative.

In one advantageous variant, the crosslinking agent is composed of a mixture of acrylamide/bisacrylamide (AA/BAA), preferably in a mass ratio of $^{19}/_1$.

In one variant of the preparation method according to the invention, the mass proportion of the AA/BAA mixture, preferably in a mass ratio of $^{19}/_1$(AA/BAA), based on the total mass of the polymerisation solution, is between 3 mass % and 8 mass %.

More particularly advantageously, the mass proportion of the AA/BAA mixture, preferably in a mass ratio of $^{19}/_1$(AA/BAA), based on the total mass of the polymerisation solution, is between 6.6 mass % and 7.3 mass %.

The polymerisation solution implemented in step (b) of the preparation method according to the invention also comprises several solvents.

These solvents may especially be selected from dodecanol (DOC), dimethylsulphoxide (DMSO) and dimethylformamide (DMF).

In one advantageous variant of the preparation method according to the invention, the polymerisation solution implemented in step (b) comprises three solvents, which are, preferentially, dodecanol, dimethylformamide and dimethylsulphoxide.

In this advantageous variant, the mass proportion of dodecanol, based on the total mass of the polymerisation solution, is between 28 mass % and 59 mass % and, preferentially, between 52.7 mass % and 58.3 mass %; the mass proportion of dimethylsulphoxide, based on the total mass of the polymerisation solution, is between 22 mass % and 53 mass % and, preferentially, between 22.8 mass % and 25.2 mass %; and the mass proportion of dimethylformamide, based on the total mass of the polymerisation solution, is between 7 mass % and 9 mass %.

The polymerisation solution implemented in step (b) of the preparation method according to the invention further comprises a radical polymerisation initiator.

This radical polymerisation initiator may especially be selected from the radical polymerisation initiators which may be used for the preparation of monolithic supports, namely azobisisobutyronitrile (AIBN), 2,2-diethoxyacetophenone (DEA), α-dialkoxyacetophenones, 2,2-dimethyl-2-hydroxyacetophenone (DARO), α-hydroxyacetophenones, benzoin methyl ether (BME), 2-methyl-4'-(methylthio)-2-morpholino-propiophenone (IRG), α-alkylaminoacetophenones or alternatively 2,2-dimethoxy-2-phenylacetophenone (DMPA).

In one variant of the preparation method according to the invention, the mass proportion of radical polymerisation initiator, based on the total mass of the polymerisation solution, is between 0.05 mass % and 0.2 mass %.

More particularly advantageously, the mass proportion of radical polymerisation initiator, based on the total mass of the polymerisation solution, is between 0.14 mass % and 0.16 mass %.

5                                                  6

In one preferential variant of the preparation method according to the invention, the polymerisation solution implements azobisisobutyronitrile (AIBN) as radical polymerisation initiator.

It should be noted that a polymerisation solution for synthesising a monolithic support comprising polyethylene glycol methacrylate phosphate, acrylamide, bisacrylamide, dodecanol, dimethylsulphoxide, dimethylformamide and azobisisobutyronitrile was very recently described in the publication by M. Araya-Farias et al. ("*A lab-on-chip for monolith-based preconcentration and electrophoresis separation of phosphopeptides*", Analyst, 2017, 142, 485-494), referenced [3], to preconcentrate phosphopeptides, which are potential biomarkers of Alzheimer's disease. To this end, $Zr^{4+}$ cations were immobilised on the surface of a phosphated monolithic support synthesised in situ and anchored into the microchannel of a commercial cross-shaped chip. The miniaturised analytical system incorporating such a monolithic support demonstrated excellent performance in terms of selectivity and enrichment factor of phosphopeptides.

Now, unexpectedly and surprisingly, the Inventors have observed that the support described in publication [3] is entirely adapted for an application other than that described in this publication, no longer for the immobilisation of $Zr^{4+}$ cations and the capture of some phosphopeptides, but for the immobilisation of $UO_2^{2+}$ cations, the capture of uranium-selectively binding proteins as well as their recovery.

In one particularly preferred embodiment, the polymerisation solution which is introduced into the internal volume of the channel(s) in step (b) of the preparation method according to the invention comprises, based on the total mass of the polymerisation solution:

from 4 mass % to 10 mass % and, advantageously, from 8.7 mass % to 9.7 mass % of polyethylene glycol methacrylate phosphate, from 3 mass % to 8 mass % and, advantageously, from 6.6 mass % to 7.3 mass % of a mixture of acrylamide/bisacrylamide, preferably in a mass ratio of $^{19}/_1$, from 28 mass % to 59 mass % and, advantageously, from 52.7 mass % to 58.3 mass % of dodecanol, from 22 mass % to 53 mass % and, advantageously, from 22.8 mass % to 25.2 mass % of dimethylsulphoxide, from 7 mass % to 9 mass % dimethylformamide, and from 0.05 mass % to 0.2 mass % and, advantageously, from 0.14 mass % to 0.16 mass % of azobisisobutyronitrile.

After step (b) of introducing the polymerisation solution into the internal volume of the channel(s) of the miniaturised analytical system, step (c) of polymerising this polymerisation solution is carried out in order to obtain a monolithic support.

This polymerisation step (c) of the preparation method according to the invention is a radical chain polymerisation, initiated by the radical polymerisation initiator.

This polymerisation step (c) is advantageously a photopolymerisation, that is a polymerisation carried out by irradiating the polymerisation solution by means of ultraviolet (UV) rays. This irradiation can especially be carried out on a localised zone of the channel.

In one advantageous variant of the preparation method according to the invention, the wavelength of the ultraviolet rays is between 320 nm and 380 nm, preferentially between 330 nm and 370 nm and, even more preferentially, is 347 nm, which is the absorption maximum of AIBN.

In one advantageous variant of the preparation method according to the invention, the duration of irradiation by means of the ultraviolet rays is between 5 min and 60 min, advantageously between 15 min and 45 min and, preferentially, is 25 min.

At the end of step (c), a monolithic support, which has been synthesised in situ and which is anchored onto the walls of the channel(s) of the miniaturised analytical system, is obtained.

The preparation method according to the invention comprises, after the polymerisation step (c), a step (d) of rinsing the monolithic support. This rinsing step (d) makes it possible to remove excess reagents from the polymerisation solution that have not reacted.

This rinsing step (d) may especially be carried out successively with alcohol and then with water, the alcohol being advantageously methanol.

The preparation method then comprises a step (e) of contacting the rinsed monolithic support, as obtained at the end of step (d), with a solution comprising the $UO_2^{2+}$ cations. In this way, a monolithic support is obtained in the internal volume of the channel(s) and on which the $UO_2^{2+}$ cations are immobilised.

In one advantageous variant of the preparation method according to the invention, the solution comprising the $UO_2^{2+}$ ions is prepared in an aqueous solution of ammonium acetate.

The monitoring of the binding of the $UO_2^{2+}$ ions to the monolithic support can advantageously be performed by coupling with an inductively coupled plasma mass spectrometer (ICP-MS).

In one advantageous variant of the preparation method according to the invention, step (e) of contacting the monolithic support with the solution comprising the $UO_2^{2+}$ cations is performed by circulating this solution comprising the $UO_2^{2+}$ cations through the monolithic support.

The preparation method according to the invention thus makes it possible to synthesise in situ a monolithic support on which the uranyl $UO_2^{2+}$ cations are immobilised, in miniaturised analytical systems whose size is far smaller, at least by a factor of 1000, than those of analytical systems formed by microbeads such as those described by publications [1] and [2].

In particular, the method according to the invention makes it possible to prepare supports on which $UO_2^{2+}$ cations are immobilised in channels whose internal diameter can advantageously be less than or equal to 300 μm and, preferentially, can be between 50 μm and 90 μm.

The reduction in scale that can be achieved with the preparation method according to the invention also makes it possible to reduce the consumption of solvents and reagents as well as the amount of reaction by-products and the treatment thereof, which is an evident advantage from an industrial standpoint. This reduction in scale is all the more advantageous for applications in the nuclear field, in that it allows a reduction in restrictions related to the handling of radioactive samples, but also a limitation of the volumes of waste and of the costs associated with their specific management.

Secondly, the present invention is concerned with a method for capturing proteins that selectively bind uranium, these proteins being contained in a biological sample.

According to the invention, this capture method comprises the following steps (i) and (ii) of:

(i) preparing, in the internal volume of at least one channel of a miniaturised analytical system, a monolithic support on which $UO_2^{2+}$ cations are immobilised, by implementing the preparation method as defined above, and (ii) at least circulating a solution containing the biological sample through the monolithic support on which $UO_2^{2+}$ cations are immobilised, obtained at the end of step (i), whereby the capture of the proteins that selectively bind uranium on the monolithic support is achieved.

In the capture method according to the invention, during step (i), a monolithic support is prepared in situ by the preparation method as defined above, it being set out that the advantageous characteristics of this preparation method, especially those relating to the details of implementation of steps (a) to (e) and those relating to the channel(s) of the miniaturised analytical system, may be taken alone or in combination.

As already described above, this monolithic support is anchored onto the inner walls of the channel(s) and comprises immobilised uranyl ions.

During the circulation step (ii), selective capture of the protein(s) which, among that or those contained in the biological sample, has/have an affinity for the $UO_2^{2+}$ ions which are immobilised on the monolithic support, takes place.

The selective capture of these proteins that selectively bind uranium is therefore performed according to the IMAC mode and this, from a biological sample whose involved amount can be drastically reduced with respect to that required for the capture by means of the support of publications [1] and [2].

Thirdly, the present invention is concerned with a method for recovering proteins that selectively bind uranium, these proteins being contained in a biological sample.

According to the invention, this method comprises the following steps (1) to (3) of:

(1) capturing the proteins that selectively bind uranium by implementing the capture method as defined above, (2) removing the unbound proteins by rinsing the monolithic support by circulating a solution containing no proteins, and (3) at least one elution step, by circulating an eluting solution through the monolithic support obtained at the end of step (2), whereby the proteins that selectively bind uranium are recovered in the eluting solution.

In the recovery method according to the invention, in step (1), the uranium-selectively binding proteins are captured by implementing the capture method as defined above, it being set out that the advantageous characteristics of this capture method may be taken alone or in combination.

These uranium-selectively binding proteins, which have been captured during step (1), are thus recovered from the monolithic support by implementing step (3), which comprises at least one elution step by means of an eluting solution.

The recovery method according to the invention is particularly simple to implement and makes it possible, by elution, to selectively recover the uranium-selectively binding proteins which have previously been captured on the monolithic support onto which $UO_2^{2+}$ cations are immobilised.

It is set out that the biological sample involved in the method for capturing uranium-selectively binding proteins and, consequently, in the method for recovering uranium-selectively binding proteins, may especially consist of protein solutions, cell extracts or biological fluids, and may especially be derived from a human neuronal cell line.

Other characteristics and advantages of the invention will become apparent upon reading the following additional description, which relates to an example of preparation of an 8 mm monolithic support on which uranyl cations are immobilised, as well as to an example making it possible to illustrate the performance of such a monolithic support for capturing and then recovering uranium-selectively binding proteins contained in a biological sample.

Of course, these examples are only given by way of illustration of the subject of the invention and are, in no way, a limitation to this subject.

DETAILED DISCLOSURE OF PARTICULAR EMBODIMENTS

A polymerisation solution for synthesising a monolithic support has been prepared from the following compounds, in the mass proportions set out below:

2.22 mg (0.15 mass %) of azobisisobutyronitrile (AIBN), 100.05 mg (6.7 mass %) of a mixture of acrylamide (AA) and bisacrylamide (BAA) (ratio $^{19}\!/_1$), 130.60 mg (8.7 mass %) of polyethylene glycol methacrylate phosphate (EGMP), 346.03 mg (23.1 mass %) of dimethylsulphoxide (DMSO), 799.93 mg (53.4 mass %) of dodecanol (DOC), and 118.80 mg (7.9 mass %) of dimethylformamide (DMF).

AIBN, AA-BAA, EGMP, DMSO, DOC, then DMF have been successively introduced into a vial and all these compounds have been mixed to obtain the polymerisation solution for synthesising the monolithic support.

After degassing, the polymerisation solution obtained was introduced into one or more channels of the four straight channels, parallel to each other and having a width of 50 μm, a depth of 50 μm and a length of 58.5 mm, of a glass analytical microsystem marketed by the company Chip-Shop.

It is set out that, before introducing this polymerisation solution, the inner surface of the channel(s) has been functionalised by a mixture comprising gamma-methacryloxy-propyltrimethoxysilane (γ-MAPS) solubilised in acetone (50/50, v/v).

After introducing the polymerisation solution into one or more channels of the four channels, the microsystem has been placed in an oven under UV radiation with a maximum wavelength of 365 nm, at 14.5 cm from the source for 25 min so as to have a power of 3.1 mW.cm$^{-2}$ in order to achieve polymerisation of the polymerisation solution.

The monolithic support thus formed in the channel(s) has been rinsed with a mixture comprising methanol and water.

A solution comprising 500 parts per billion (ppb) of uranyl ions in ammonium acetate buffer at a molar concentration of ammonium acetate of between 25 mmol/L and 50 mmol/L and a pH of between 4 and 5 has been prepared.

This solution has then been circulated through the monolithic support synthesised in situ and anchored onto the walls of the channel(s) of the microsystem, for 60 min, at a flow rate of 0.24 mL/h (4 μL/min) so as to immobilise uranyl ions on the surface of the monolithic support.

The immobilisation efficiency of the uranyl ions is determined using an inductively coupled plasma mass spectrometer (ICP-MS).

This step can be carried out off-line by recovering fractions. But this step can advantageously be carried out on-line, that is continuously, by coupling the microsystem with the mass spectrometer via a micro-nebuliser. In the case of the present example, 50 ng of uranium have been bound onto the 8 mm monolithic support.

In the case where the mass spectrometer is a triple quadrupole ICP, the signal of phosphorus and/or of sulphur contained in the proteins can also be monitored in addition to that of uranium, when monitoring the capture of proteins.

The ability to monitor both the uranyl ions and their target molecules is a considerable advantage, this making it possible to determine both the efficiency of immobilisation of these ions on the monolithic support and its capacity to capture target molecules, through interaction with the immobilised ions. As an example, the amount of the apotransferrin protein, which is captured by this monolithic support on which the uranyl ions are immobilised and recovered, is 0.75 µg.

Table 1 below shows the amount of uranium immobilised on the monolithic support prepared by the method according to the invention, as well as the amount of apotransferrin recovered following its capture by this same support, by comparison with the amounts obtained with the reference support formed by the microbeads as described in publication [1].

TABLE 1

|  | Microbead support (reference) | Monolithic support (according to the invention) |
| --- | --- | --- |
| Volume of support | 50 µL of a solution of 1.1 g of microbeads/mL | 16 nL (8 mm × 50 µm × 50 µm) |
| Amount of uranium immobilised | 5.95 mg | 50 ng |
| Amount of apotransferrin eluted | 40 µg | 0.75 µg |

REFERENCES

[1] C. Basset et al., *Journal of Chromatography A*, 2008, 1185, p. 233-240

[2] A. Dedieu et al., *Journal of Chromatography A*, 2009, 1216, p. 5365-5376

[3] M. Araya-Farias et al., *Analyst*, 2017, 142, p. 485-494

What is claimed is:

1. A method for preparing, in an internal volume of at least one channel of a miniaturised analytical system, a monolithic support on which $UO_2^{2+}$ cations are immobilised, which method comprises the following successive steps (a) to (e) of:

(a) activating the inner surface of the channel(s);

(b) introducing a polymerisation solution for synthesising a monolithic support into the internal volume of the channel(s), the polymerisation solution comprising:
a monomer comprising a phosphate group,
at least one crosslinking agent
several solvents, and
a radical polymerisation initiator;

(c) polymerising the polymerisation solution obtained in step (b), whereby a monolithic support anchored onto the walls of the channel(s) is obtained;

(d) rinsing the monolithic support obtained in step (c); and (e) contacting the rinsed monolithic support obtained in step (d) with a solution comprising $UO_2^{2+}$ cations, whereby a monolithic support on which the $UO_2^{2+}$ cations are immobilized is obtained.

2. The method according to claim 1, wherein the monomer comprising a phosphate group is a methacrylate monomer.

3. The method according to claim 1, wherein the crosslinking agent is consisting of a mixture of acrylamide/bisacrylamide.

4. The method according to claim 1, wherein the solvents are selected from dodecanol, dimethylformamide and dimethylsulphoxide.

5. The method according to claim 1, wherein the radical polymerisation initiator is azobisisobutyronitrile (AIBN).

6. The method according to claim 5, wherein the polymerisation solution comprises, based on the total mass of the polymerisation solution:
from 0.05 mass % to 0.2 mass % of azobisisobutyronitrile,
from 3 mass % to 8 mass % of acrylamide and bisacrylamide,
from 4 mass % to 10 mass % of polyethylene glycol methacrylate phosphate,
from 22 mass % to 53 mass % of dimethylsulphoxide,
from 28 mass % to 59 mass % of dodecanol, and
from 7 mass % to 9 mass % dimethylformamide.

7. The method according to claim 1, wherein the polymerisation step (c) is carried out by irradiation by means of ultraviolet rays.

8. The method according to claim 7, wherein, in step (c), the duration of irradiation by means of the ultraviolet rays is between 5 min and 60 min.

9. The method according to claim 1, wherein the rinsing step (d) is carried out successively with an alcohol and then with water.

10. The method according to claim 1, wherein, the channel(s) being made of glass, the activation step (a) is carried out by silanisation.

11. The method according to claim 1, wherein the internal diameter of the channel(s) is less than or equal to 300 µm.

12. The method according to claim 1, wherein the solution comprising the $UO_2^{2+}$ cations is prepared in an aqueous solution of ammonium acetate.

13. The method according to claim 1, wherein step (e) of contacting the monolithic support with the solution comprising the $UO_2^{2+}$ cations is carried out by circulating this solution comprising the $UO_2^{2+}$ cations on the monolithic support.

14. A method for capturing proteins that selectively bind uranium, these proteins being contained in a biological sample, this method comprising the following steps (i) and (ii) of:

(i) preparing, in an internal volume of at least one channel of a miniaturised analytical system, a monolithic support on which UO22+cations are immobilised, by implementing the preparation method according to claim 1, and (ii) at least circulating a solution containing the biological sample through the monolithic support on which $UO_2^{2+}$ cations are immobilised, obtained at the end of step (i), whereby the capture of the proteins that selectively bind uranium on the monolithic support is achieved.

15. A method for recovering proteins that selectively bind uranium, these proteins being contained in a biological sample, this method comprising the following steps (1) to (3) of:

(1) capturing the proteins that selectively bind uranium by implementing the capture method of claim 14, (2) removing the unbound proteins by rinsing the monolithic support by circulating a solution containing no proteins, and (3) at least one elution step, by circulating an eluting solution through the monolithic support obtained at the end of step (2), whereby the proteins that selectively bind uranium are recovered in the eluting solution.

16. The method according to claim 2, wherein the monomer comprising a phosphate group is polyethylene glycol methacrylate phosphate.

17. The method according to claim 7, wherein the wavelength of these ultraviolet rays is between 320 nm and 380 nm.

18. The method according to claim 9, wherein the alcohol is methanol.

19. The method according to claim 10, wherein the activation step (a) is carried out by means of gamma-methacryloxypropyltrimethoxysilane (γ-MAPS) as silanising agent.

20. The method according to claim 11, wherein the internal diameter of the channel(s) is between 50 μm and 90 μm.

* * * * *